US012539372B2

(12) United States Patent
Carpenter

(10) Patent No.: US 12,539,372 B2
(45) Date of Patent: Feb. 3, 2026

(54) MEDICAMENT DELIVERY DEVICE COMPONENT OR ADD-ON MODULE FOR MEDICAMENT DELIVERY DEVICE

(71) Applicant: SHL MEDICAL AG, Zug (CH)

(72) Inventor: Lucas Carpenter, New Taipei (TW)

(73) Assignee: SHL Medical AG, Zug (CH)

( * ) Notice: Subject to any disclaimer, the term of this patent is extended or adjusted under 35 U.S.C. 154(b) by 725 days.

(21) Appl. No.: 17/915,077

(22) PCT Filed: May 14, 2021

(86) PCT No.: PCT/EP2021/062849
§ 371 (c)(1),
(2) Date: Sep. 27, 2022

(87) PCT Pub. No.: WO2021/244835
PCT Pub. Date: Dec. 9, 2021

(65) Prior Publication Data

US 2023/0149638 A1 May 18, 2023

(30) Foreign Application Priority Data

Jun. 4, 2020 (EP) .................................... 20178240

(51) Int. Cl.
*A61M 5/42* (2006.01)
*A61M 5/31* (2006.01)
*A61M 5/32* (2006.01)

(52) U.S. Cl.
CPC ............ *A61M 5/42* (2013.01); *A61M 5/3134* (2013.01); *A61M 5/3293* (2013.01)

(58) Field of Classification Search
CPC .... A61M 5/42; A61M 5/3134; A61M 5/3293; A61M 5/422; A61M 5/425
See application file for complete search history.

(56) References Cited

U.S. PATENT DOCUMENTS 5,609,577 A 3/1997 Haber et al.
6,537,242 B1 * 3/2003 Palmer .............. A61M 37/0015
600/583

(Continued)

FOREIGN PATENT DOCUMENTS

DE 102004025651 A1 12/2005
EP 1171036 B1 7/2005

(Continued)

OTHER PUBLICATIONS

International Search Report and Written Opinion for Int. App. No. PCT/EP2021/062849, mailed May 28, 2021.

(Continued)

*Primary Examiner* — Tasnim Mehjabin Ahmed
(74) *Attorney, Agent, or Firm* — McDonnell Boehnen Hulbert & Berghoff LLP

(57) ABSTRACT

The disclosure concerns a device for alleviating injection pain, the device can have an attachment portion for attachment to a medicament delivery device, a flexible arm extending from a first end attached to the attachment portion to a second end distal from the attachment portion, and a plurality of protrusions attached to the flexible arm, wherein the device is a medicament delivery device component or a medicament delivery device add-on. A medicament delivery device comprising such a device and corresponding methods are also described.

18 Claims, 1 Drawing Sheet

(56) References Cited

U.S. PATENT DOCUMENTS

| | | | | |
|---|---|---|---|---|
| 10,398,854 | B2 | 9/2019 | Fenster et al. | |
| 10,478,569 | B2 | 11/2019 | Sealfon et al. | |
| 10,485,932 | B2 | 11/2019 | Cowe et al. | |
| 2007/0021716 | A1 | 1/2007 | Hansen | |
| 2012/0253314 | A1 | 10/2012 | Harish et al. | |
| 2015/0258284 | A1* | 9/2015 | Fenster | A61M 5/3205 604/115 |
| 2016/0271341 | A1 | 9/2016 | Chanie et al. | |
| 2018/0326163 | A1* | 11/2018 | Bailey | A61M 5/425 |

FOREIGN PATENT DOCUMENTS

| | | | |
|---|---|---|---|
| EP | 2886148 | A1 | 6/2015 |
| EP | 2647337 | B1 | 10/2015 |
| JP | 2012-239824 | A | 12/2012 |
| WO | 01/93931 | A1 | 12/2001 |

OTHER PUBLICATIONS

TickleFLEX Insulin Injection [Retrieved on Sep. 26, 2022] from the Internet: https://www.tickleflex.com/#features.

* cited by examiner

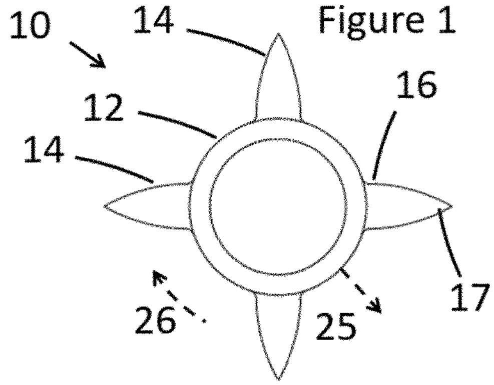
Figure 1
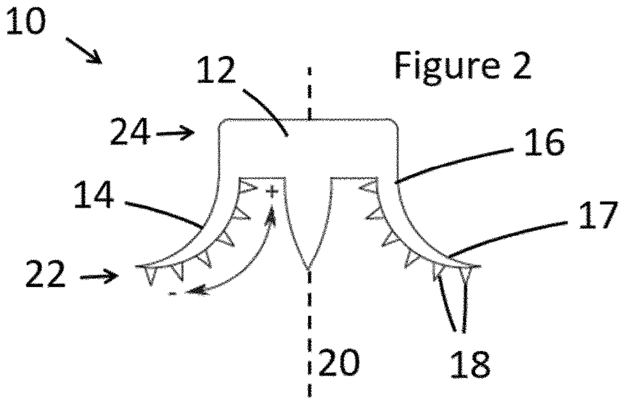
Figure 2
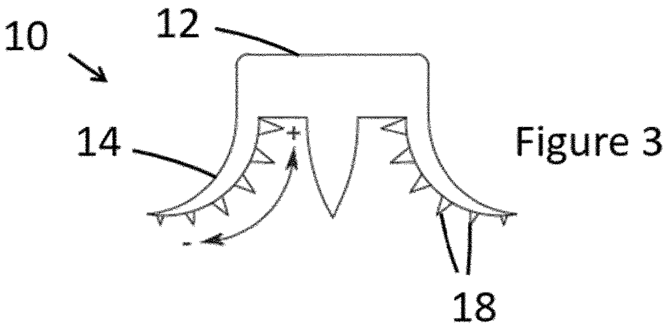
Figure 3
Figure 4
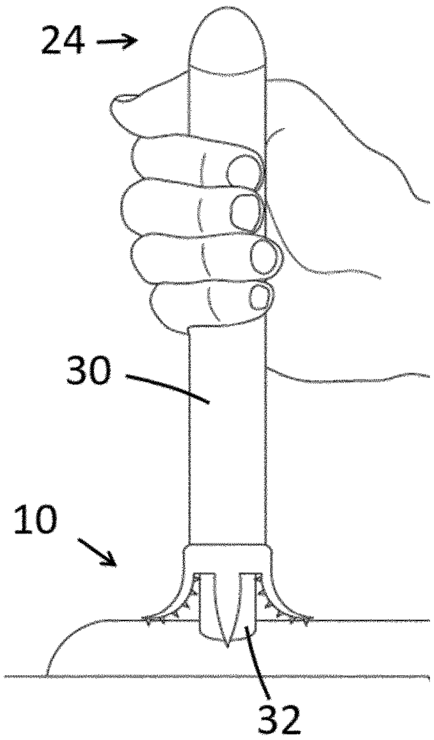
Figure 5
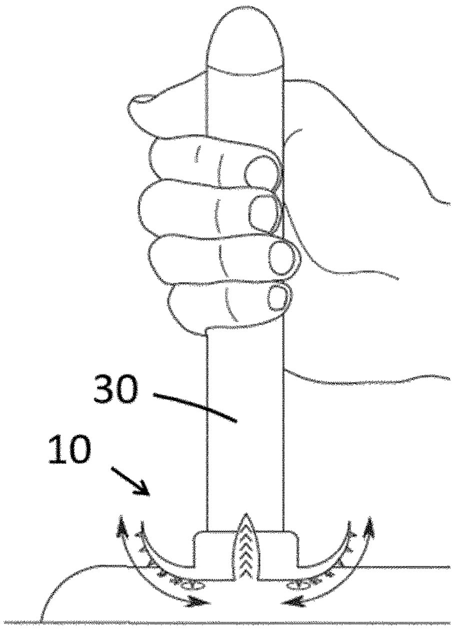

MEDICAMENT DELIVERY DEVICE COMPONENT OR ADD-ON MODULE FOR MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2021/062849 filed May 14, 2021, which claims priority to European Patent Application No. 20178240.6 filed Jun. 4, 2020. The entire disclosure contents of these applications are herewith incorporated by reference into the present application.

TECHNICAL FIELD

The present disclosure concerns medicament delivery device components or medicament delivery device add-ons, and particularly concerns medicament delivery device components or medicament delivery device add-ons for alleviating injection pain.

BACKGROUND

Although medicament delivery devices such as pen injectors and autoinjectors can make a significant positive difference to the well-being of patients and caregivers that use them, they can still suffer from the drawback of causing pain at the injection site. The applicant has appreciated that there is further potential for alleviation of this pain.

SUMMARY

The present disclosure is defined by the appended claims, to which reference should now be made.

In the present disclosure, when the term "distal direction" is used, this refers to the direction pointing away from the dose delivery site during use of the medicament delivery device. When the term "distal part/end" is used, this refers to the part/end of the delivery device, or the parts/ends of the members thereof, which under use of the medicament delivery device is/are located furthest away from the dose delivery site. Correspondingly, when the term "proximal direction" is used, this refers to the direction pointing towards the dose delivery site during use of the medicament delivery device. When the term "proximal part/end" is used, this refers to the part/end of the delivery device, or the parts/ends of the members thereof, which under use of the medicament delivery device is/are located closest to the dose delivery site.

Further, the terms "longitudinal", "longitudinally", "axially" and "axial" refer to a direction extending from the proximal end to the distal end and along the device or components thereof, typically in the direction of the longest extension of the device and/or component.

Similarly, the terms "transverse", "transversal" and "transversally" refer to a direction generally perpendicular to the longitudinal direction.

A first aspect of the present disclosure concerns a device for alleviating injection pain, the device comprising an attachment portion for attachment to a medicament delivery device, a flexible arm extending from a first end attached to the attachment portion to a second end distal from the attachment portion, and a plurality of protrusions attached to the flexible arm. Preferably, the device is a medicament delivery device component or a medicament delivery device add-on. Such a device can reduce injection (drug delivery) discomfort. In particular, such a device can reduce injection pain by skin stimulation, distracting from the injection and reducing the subjective pain and/or discomfort of injection, particularly during the injection itself.

Preferably, the width of the second end of the flexible arm is thinner than the width of the first end of the flexible arm. Preferably, the width of the flexible arm tapers from the first end to the second end. The flexible arm is more flexible at the second end than at the first end. Such configurations can result in provision of an increasing pressure applied by the device around the injection site as the device is pushed towards the injection site.

Preferably the protrusions are distributed along the flexible arm between the first end and the second end, for example along at least half of the length of the flexible arm, or more preferably along at least three-quarters of the length of the flexible arm. Preferably, the protrusions proximal to the first end of the flexible arm are longer than the protrusions proximal to the second end of the flexible arm. Such configurations can result in provision of an increased sensation applied by the device around the injection site as the device is pushed towards the injection site.

Preferably, the device extends along an axis from a proximal end to a distal end, wherein the first end of the flexible arm is closer to the distal end than the second end of the flexible arm. Preferably, the second end of the flexible arm is further from an axis than the first end of the flexible arm. Preferably, wherein the flexible arm describes an arc. Such configurations can help the arms spread reliably as the device is pushed towards the injection site.

Preferably, the device comprises a plurality of flexible arms, each flexible arm comprising a plurality of protrusions. This can provide a greater effect than a single arm. Preferably, the device is a medicament delivery device add-on and the attachment portion is removably attachable to a medicament delivery device.

A second aspect of the present disclosure concerns a medicament delivery device comprising the device described above. Preferably, the flexible arm is closer than the attachment portion to a proximal end of the medicament delivery device.

Generally, all terms used in the claims are to be interpreted according to their ordinary meaning in the technical field, unless explicitly defined otherwise herein. All references to a/an/the element, apparatus, member, component, means, etc. are to be interpreted openly as referring to at least one instance of the element, apparatus, member component, means, etc., unless explicitly stated otherwise.

BRIEF DESCRIPTION OF THE DRAWINGS

Embodiments of the present disclosure will now be described by way of example only and with reference to the accompanying drawings, in which:

FIG. 1 shows an example device.

FIG. 2 shows a side view of one embodiment of the device of FIG. 1.

FIG. 3 shows a side view of another embodiment of the device of FIG. 1.

FIG. 4 shows a side view of an autoinjector comprising the device of FIG. 1 before carrying out an injection.

FIG. 5 shows a side view of the autoinjector of FIG. 4 whilst carrying out an injection.

DETAILED DESCRIPTION

FIGS. 1 and 2 show a device 10 for alleviating injection pain, the device comprising an attachment portion 12 for attachment to a medicament delivery device, a flexible arm 14 extending from a first end 16 attached to the attachment portion to a second end 17 distal from the attachment portion, and a plurality of protrusions 18 attached to the flexible arm. The device is a medicament delivery device component or a medicament delivery device add-on.

FIG. 2 shows the device 10 relative to an axis 20 (central axis), with the device 10 extending from a proximal end 22 to a distal end 24. In FIG. 2, the protrusions are all the same size. FIG. 3 shows a similar device, but with protrusions of varying sizes, with protrusions closer to the attachment portion being larger than protrusions further from the attachment portion.

FIGS. 4 and 5 show the device 10 attached to a medicament delivery device, in this case an autoinjector 30. A medicament delivery member shield 32 of the autoinjector can also be seen. FIG. 4 shows the autoinjector prior to injection and FIG. 5 shows the autoinjector during injection.

To use the device 10, the device is first attached to a medicament delivery device, for example by an end user prior to use of a medicament delivery device or by a manufacturer during manufacture of the medicament delivery device, particularly where the device is a medicament delivery device component. An injection can then be carried out as normal with the medicament delivery device. As the device is pressed against the skin, the flexible arms flex outwards away from the axis 20, and the protrusions 18 rub across the skin, providing a sensation that can distract from injection pain. Once an injection has been completed, the medicament delivery device can be removed from the skin. If the flexible arms are plastically deformable, they can then return back to (roughly) their original position, allowing for multiple uses of the device (either on the same medicament delivery device if the medicament delivery device is reusable, and/or on another medicament delivery device if the device is removable).

The device described herein can be considered to be a pain alleviation device, as it can alleviate injection pain. The device could be a medicament delivery add-on in its own right, as shown in the examples in the Figures, or it could be a medicament delivery device component, such as a medicament delivery member guard or a housing that includes the flexible arms described herein.

Various designs are possible for the attachment portion 12. For example, the attachment portion could attach with a friction lock (as shown in the examples in the Figures), or could have a clip, a lock, or another kind of attachment. The attachment portion could also be adhered to the medicament delivery device. The attachment could be permanent or removable—that is, the device could be designed to be removable or to be permanently attached to a medicament delivery device. Providing a removable attachment would allow for the attachment to be reused on another medicament delivery device.

In examples where the device is a medicament delivery device component, the attachment portion would attach the component to the rest of the medicament delivery device. The component could be a housing or a medicament delivery member guard, for example.

The attachment portion would typically be a distal portion of the device. The attachment portion is shown as a ring in the example in FIGS. 1 and 2, though it could have various other shapes. The attachment portion is shown with a circular cross-section perpendicular to the axis 20 in FIG. 1, though it could have a different shaped cross-section such as a triangular, square or irregularly shaped cross-section. The attachment portion could also be flexible to allow attachment to different device diameters and shapes, which has the advantage of allowing the device to be used with various different medicament delivery devices. Alternatively, the attachment portion could be rigid; this could be beneficial in that it could limit use to a specific device or devices, thereby avoiding use of the device on the wrong type of medicament delivery device.

Various designs are also possible for the arms 14. Four arms are shown on the examples in the Figures, though 1, 2, 3 or more arms could alternatively be provided. The arms shown are all the same, though the arms could also differ from one another. The arms are shown tapering from a wider part at the end attached to the attachment portion (first end) down to a thinner part at the end distal from the attachment portion (second end), though the arms could also be the same width for their full length. The arms are shown tapering by variation in width in both a radial direction 25 relative to the axis and a circumferential direction relative to the axis, though the arms could alternatively only taper in the radial direction 25 or in the circumferential direction 26. The arms are shown as arc-shaped (describe an arc) when viewed from the side (i.e. the shape such as that shown for two of the arms in FIG. 2, or in other words, when a cross-section along the perpendicular axis and through an arm is taken and viewed in a direction perpendicular to the axis 20, the arms are arc-shaped), though they could alternatively be another shape, such as straight. The second end is shown as being further from the axis than the first end, though this is also optional, and the arms could be parallel to the axis, for example.

Various options are also possible for the protrusions 18. The Figures show six protrusions on each arm, though more or fewer protrusions could be provided. The protrusions are shown evenly distributed along the length of the arms, though the protrusions could be unevenly spaced and/or only provided along part of the length of the arms. The protrusions are shown as a tapered spike with a sharp end, but could also have other shapes and/or could be blunt ended protrusions (e.g. a frustoconical shape or a cylindrical shape). FIG. 2 shows an example with the protrusions all the same size, and FIG. 3 shows longer protrusions closer to the first end of the flexible arm, with the protrusion length reducing as a function of distance from the first end of the flexible arm. Irregular patterns of protrusion length and width are also possible. The provision of protrusions in general is also optional.

The example shown in FIGS. 4 and 5 shows an autoinjector, but the device could be used on other medicament delivery devices such as pen injectors, for example. A suitable autoinjector could include features such as an outer housing, a medicament delivery member guard, a syringe comprising a medicament barrel and a medicament delivery member, and/or a powerpack, for example.

Various modifications to the embodiments described are possible and will occur to those skilled in the art without departing from the present disclosure which is defined by the following claims.

The invention claimed is:

1. A device for alleviating injection pain, the device comprising:

an attachment portion for attachment to a medicament delivery device, a flexible arm extending from a first end attached to the attachment portion to a second end distal from the attachment portion, wherein the second end flexes distally away from a longitudinal axis of the medicament delivery device, and a plurality of protrusions attached to the flexible arm, wherein the plurality of protrusions are configured to move laterally across a medicament delivery site when pressed down onto the medicament delivery site.

2. The device of claim 1, wherein the width of the second end of the flexible arm is thinner than the width of the first end of the flexible arm.

3. The device of claim 1, wherein the width of the flexible arm tapers from the first end to the second end.

4. The device of claim 1, wherein the flexible arm is more flexible at the second end than at the first end.

5. The device of claim 1, wherein the protrusions are distributed along the flexible arm between the first end and the second end.

6. The device of claim 5, wherein the protrusions proximal to the first end of the flexible arm are longer than the protrusions proximal to the second end of the flexible arm.

7. The device of claim 5, wherein the device extends along an axis from a proximal end to a distal end, wherein the first end of the flexible arm is closer to the distal end than the second end of the flexible arm.

8. The device of claim 1, wherein the second end of the flexible arm is further from an axis than the first end of the flexible arm.

9. The device of claim 1, wherein the flexible arm describes an arc.

10. The device of claim 1, comprising a plurality of flexible arms, each flexible arm comprising a plurality of protrusions.

11. The device of claim 1, wherein the device is a medicament delivery device component or a medicament delivery device add-on.

12. The device of claim 1, wherein the device is a medicament delivery device add-on and the attachment portion is removably attachable to a medicament delivery device.

13. A medicament delivery device comprising the device of claim 1.

14. A reusable flexible device for attachment to a medicament delivery device, the flexible device comprising:

a distal end configured with a reusable connector for removable attachment to a proximal end of the medicament delivery device;

a flexible arm extending from a proximal end portion of the connector, where the flexible arm has a first end that is attached to the connector and that tapers and extends away from the connector terminating at a second end; and a plurality of protrusions extending from an inner surface of the flexible arm, wherein the second end is free to flex radially relative to the connector and the protrusions vary in length along the inner surface prior to contact with a medicament delivery site.

15. The flexible device of claim 14, wherein the flexible arm is arc-shaped.

16. The flexible device of claim 14, wherein the second end of the flexible arm is positioned proximal to the first end prior to contact with the medicament delivery site and are distal to the first end when the flexible device is pressed against the medicament delivery site.

17. The device of claim 14, wherein the flexible arm comprises one of a plurality of flexible arms.

18. The device of claim 17, wherein the plurality of flexible arms comprises three flexible arms.

* * * * *